United States Patent
Blank et al.

(10) Patent No.: US 10,370,408 B2
(45) Date of Patent: Aug. 6, 2019

(54) METHOD FOR PURIFICATION OF A DNASE OR RNASE PROTEIN FROM A SAMPLE

(71) Applicants: JHL BIOTECH, INC., Grand Cayman (KY); Gregory Scott Blank, Menlo Park, CA (US)

(72) Inventors: Gregory Scott Blank, Menlo Park, CA (US); Jiun-Liang Lin, Hualien (CN)

(73) Assignee: JHL Biotech, Inc., Grand Cayman (KY)

( * ) Notice: Subject to any disclaimer, the term of this patent is extended or adjusted under 35 U.S.C. 154(b) by 0 days.

(21) Appl. No.: 15/321,016

(22) PCT Filed: Jun. 25, 2015

(86) PCT No.: PCT/US2015/037705
§ 371 (c)(1),
(2) Date: Dec. 21, 2016

(87) PCT Pub. No.: WO2015/200645
PCT Pub. Date: Dec. 30, 2015

(65) Prior Publication Data
US 2017/0198008 A1    Jul. 13, 2017

Related U.S. Application Data

(60) Provisional application No. 62/017,153, filed on Jun. 25, 2014.

(51) Int. Cl.
| | |
|---|---|
| *C07K 1/16* | (2006.01) |
| *C12N 9/22* | (2006.01) |
| *B01D 15/38* | (2006.01) |
| *B01D 15/42* | (2006.01) |
| *B01D 15/36* | (2006.01) |
| *C07K 1/18* | (2006.01) |

(52) U.S. Cl.
CPC ............ *C07K 1/165* (2013.01); *B01D 15/361* (2013.01); *B01D 15/3847* (2013.01); *B01D 15/426* (2013.01); *C07K 1/18* (2013.01); *C12N 9/22* (2013.01)

(58) Field of Classification Search
None
See application file for complete search history.

(56) References Cited

U.S. PATENT DOCUMENTS

| | | | | |
|---|---|---|---|---|
| 6,489,447 B1 * | 12/2002 | Basey | ...................... | C07K 1/18 530/387.1 |
| 7,531,645 B2 * | 5/2009 | Basey | ...................... | C07K 1/18 530/416 |
| 2003/0077267 A1 | 4/2003 | Frenz et al. | | |
| 2008/0207879 A1 | 8/2008 | Mitterer et al. | | |
| 2009/0042266 A1 | 2/2009 | Vehmaanpera et al. | | |
| 2010/0022757 A1 | 1/2010 | Eon-Duval et al. | | |
| 2010/0075376 A1 * | 3/2010 | Rasmussen | ............... | C12N 1/08 435/69.1 |
| 2013/0280788 A1 | 10/2013 | Skudas | | |

FOREIGN PATENT DOCUMENTS

| | | | |
|---|---|---|---|
| EP | 2027875 A1 | | 2/2009 |
| SU | 1100308 A1 | * | 6/1984 |
| WO | WO 2009/007451 A1 | | 1/2009 |
| WO | WO 2013/067301 A1 | | 5/2013 |
| WO | WO 2015/200645 A1 | | 12/2015 |

OTHER PUBLICATIONS

Extended European Search Report for European Application No. 15812350.5, dated Jan. 29, 2018, 8 pages.
PCT/US2015/037705, International Search Report and Written Opinion dated Oct. 1, 2015, 9 pages.
PCT/US2015/037705, International Preliminary Report on Patentability dated Dec. 27, 2016, 7 pages.
Funakoshi, A., et al., "Simple purification and properties of bovine pancreatic deoxyribonuclease I." J Biochem. (1980); 88(4): 1113-1118.

* cited by examiner

*Primary Examiner* — Christian L Fronda
(74) *Attorney, Agent, or Firm* — The Webb Law Firm

(57) ABSTRACT

The present disclosure provides compositions and methods for purifying a protein such as DNase using a chromatographic process. The methods include a single chromatographic step and the use of high concentration salt buffers.

25 Claims, 2 Drawing Sheets

METHOD FOR PURIFICATION OF A DNASE OR RNASE PROTEIN FROM A SAMPLE

CROSS REFERENCE TO RELATED APPLICATIONS

This application claims priority to U.S. Provisional Application No. 62/017,153, filed Jun. 25, 2014, which is hereby incorporated by reference in its entirety for all purposes.

BACKGROUND

Proteins, including enzymes such as deoxyribonuclease (DNase) that are useful for investigational and commercial uses, may be produced using recombinant methodologies or purified from cells in which they are naturally produced. In either case, purification of such proteins is an important step in generating proteins suitable for use. DNase and other proteins are commonly purified using chromatography methods, including methods that involve the use of more than one chromatography column. However, there is a clear unmet need in the art for methods of purification of enzymes such as DNase that are convenient and provide both high purity and high yield.

SUMMARY OF THE INVENTION

The present disclosure provides methods for purification of a protein from a sample comprising loading the sample onto a chromatography column and washing the column with at least one buffer having very high conductivity. In some embodiments, the wash buffer has a conductivity of about 50 mS/cm, about 60 mS/cm, about 70 mS/cm, about 80 mS/cm, or higher. In further embodiments, the protein is eluted from the column with an elution buffer following the wash with the very high conductivity buffer. In yet further embodiments, the elution buffer also has very high conductivity. In still further embodiments, the elution buffer has a conductivity of about 50 mS/cm, about 60 mS/cm, about 70 mS/cm, about 80 mS/cm, or higher.

In some embodiments, the wash buffer having very high conductivity comprises a salt selected from the group consisting of $(NH_4)_2SO_4$, $Na_2SO_4$, and $CH_3COONa$. In further embodiments, the wash buffer comprises 0.8 M $(NH_4)_2SO_4$. In some embodiments, the elution buffer comprises a salt selected from the group consisting of NaCl, KCl, and NaOAc. In further embodiments, the elution buffer comprises 1 M NaCl.

In some embodiments, the method comprises at least two washing steps. In further embodiments, the method comprises a first washing step wherein the column is washed with a buffer having low conductivity. In further embodiments, the buffer having low conductivity has conductivity of about 2 mS/cm or about 1 mS/cm. In such embodiments, the second washing step comprises washing the column with a very high conductivity buffer. In some embodiments, the method comprises three washing steps, comprising (i) washing the column with a first buffer having low conductivity; (ii) washing the column with a second buffer having very high conductivity; and (iii) washing the column with a third buffer having low conductivity. In some embodiments, the first and the third washing steps use the same buffer. In some embodiments, one or more of the buffers comprise $CaCl_2$. In further embodiments, the buffers comprise 1 mM $CaCl_2$.

In some embodiments, the protein of interest is any protein. In further embodiments, the protein is any protein that is produced by a cell. The cell may naturally produce the protein, or the cell may be genetically altered to express the protein of interest. Accordingly, in some embodiments, the sample is harvested from a cell culture and loaded onto the column. In some embodiments, the protein is an enzyme, such as DNase or RNase. In particular embodiments, the protein is a recombinant DNase.

In some embodiments, the chromatography column is an ion exchange column such as an anion exchange column or a cation exchange column. In some embodiments, the chromatography column is a mixed mode chromatography column, for example, the mixed mode chromatography column is a multimodal anion exchanger, such as a Capto Adhere column.

In some embodiments, the sample loaded onto the chromatography column has a pH of between about 5.0 and about 9.0, or between about 6.0 and about 8.0. In some embodiments, the pH of the loaded sample is about 7.0. In some embodiments, the pH of the loaded sample is about the same as the pI of the protein in the sample. In other embodiments, the pH of the loaded sample is higher than the pI of the protein. For example, in some embodiments, the pH is between about 5.0 and about 9.0 and the pI of the protein of interest is about 2.5 to about 4.5. In particular embodiments, the protein is DNase and the pH of the loaded sample is between about 5.0 and about 9.0.

In some embodiments, the pH of the high conductivity wash buffer, the low conductivity wash buffer, and/or the elution buffer is between about 5.0 and about 9.0. In further embodiments, the pH of the high conductivity wash buffer, the low conductivity wash buffer, and/or the elution buffer is between about 6.0 and about 8.0. In further embodiments, pH of the high conductivity wash buffer, the low conductivity wash buffer, and/or the elution buffer is about 7.0.

In one aspect, the present disclosure provides method for purifying a protein from a sample comprising a detergent to the sample prior to loading the sample onto the chromatography column. The detergent may be selected from the group consisting of Triton X-100, sodium dodecyl sulfate (SDS), sodium tetradecyl sulfate, sodium hexadecyl sulfate, sodium deoxycholate, polyoxyethylene sorbitan monooleate, and NP40. In some embodiments, the detergent is Triton X-100, and the final concentration of the detergent in the sample is from about 0.1% to about 1%, or about 0.5%.

In some embodiments, the methods provided herein further comprise assessing the purity of the protein using methods known in the art such as, for example, SDS-Page analysis.

In one aspect, the present disclosure provides methods for purification of DNase from a cell culture sample, the method comprising (i) collecting the harvested cell culture fluid (HCCF) from a cell expressing DNase, (ii) adding a detergent to the HCCF sample, (iii) loading the sample onto a mixed mode chromatography column (iv) washing the column with a first wash buffer comprising 1 mM $CaCl_2$, (v) washing the column with a second wash buffer comprising 0.8 M $(NH_4)_2SO_4$ and 1 mM $CaCl_2$, and (vi) eluting the DNase from the column with an elution buffer comprising 1.0 M NaCl and 1 mM $CaCl_2$. In further embodiments, the method further comprises a third washing step between steps (v) and (vi) comprising washing the column with a wash buffer comprising 1 mM $CaCl_2$.

In some embodiments, the present disclosure provides a reagent combination or a kit. In some embodiments, the reagent combination or kit comprises a very high conductivity wash buffer as described herein. In some embodiments, the reagent combination or kit comprises both a very high conductivity wash buffer and a very high conductivity elution buffer as described herein. In further embodiments, the reagent combination or kit comprises a wash buffer having a conductivity of about 80 mS/cm or more and an elution buffer having a conductivity of about 80 mS/cm or more. In further embodiments, the wash buffer comprises about 0.8 M $(NH_4)_2SO_4$, and the elution buffer comprises about 1 M NaCl. In yet further embodiments, the wash buffer and the elution buffer each comprise 1 mM $CaCl_2$.

DETAILED DESCRIPTION OF THE INVENTION

Figure 1:
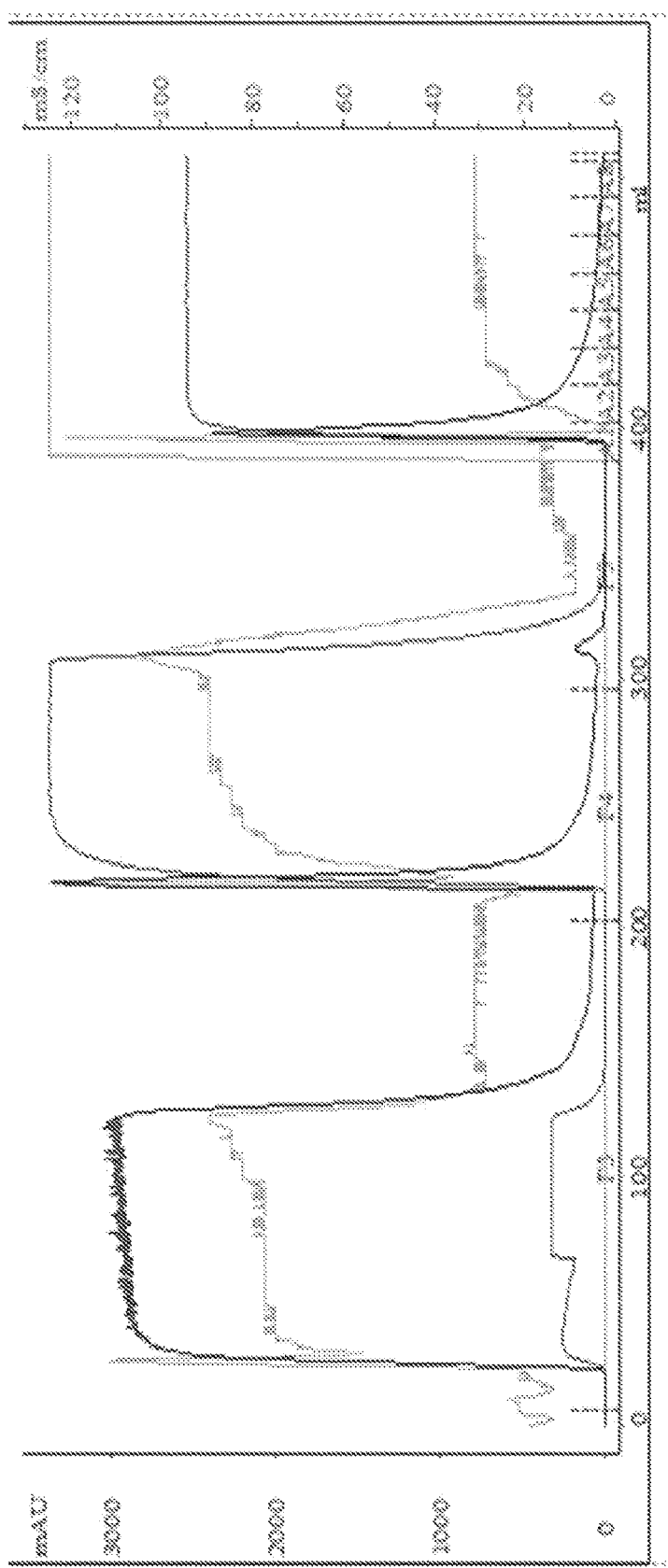
FIG. 1 is a chromatogram showing purification of DNase from a HCCF sample.

In one aspect, the present disclosure provides chromatographic methods for purifying a protein from a sample. Unexpectedly, the present inventors found that high concentration salt buffers can be used to purify proteins via chromatography. In some embodiments, the present disclosure provides that proteins may be purified from a sample by directly loading the sample onto a chromatography column. In further embodiments, loading is followed by washing and/or elution steps using high concentration salt buffers. Thus, in some embodiments, the methods provided herein advantageously allow for purification of a protein from a sample without the need to significantly alter the characteristics or components of the sample containing the protein, and/or with minimal adjustment to the chromatography column. For example, the methods provided herein allow for purification of a protein from a sample without the need for to alter the conductivity, pH, or other characteristics of the loaded sample, and without the need for ultrafiltration, diafiltration, or dilution of the sample containing the protein.

In some embodiments, the present invention provides methods for purification of proteins by chromatography using one or more high concentration salt buffers having very high conductivity. In some embodiments, the method comprises at least two washing steps, one step to remove unbound impurities, the other step to remove bound impurities. In further embodiments, the method comprises a first wash step using a high salt buffer having low conductivity to remove unbound impurities; a second wash step using a high salt buffer having very high conductivity to remove bound impurities without eluting the protein of interest; and an elution step using a high salt buffer having high conductivity that elutes the product from the column.

In some embodiments, the present disclosure provides methods for purification of proteins by chromatography comprising loading a sample comprising the protein directly onto a chromatography column, washing the column with a high salt buffer having very high conductivity, and eluting the protein from the column with a high salt buffer having very high conductivity. Thus, in some embodiments, the present disclosure provides methods for obtaining highly purified proteins using a single chromatographic step.

The methods provided herein may be used to purify any protein, including proteins produced naturally in a cell and proteins produced in a cell using recombinant methodologies. In some embodiments, the protein is an enzyme. In further embodiments, the enzyme is a deoxyribonuclease (DNase). In some embodiments, the buffers used in the methods provided herein comprise $CaCl_2$, which is essential for DNase activity. In other embodiments, the enzyme is ribonuclease (RNase).

In some embodiments, the sample containing the protein is directly loaded onto the column under high conductivity. For example, in some embodiments, the sample containing the protein is loaded onto the column under conductivity of over about 8 mS/cm, over about 9 mS/cm, over about 10 mS/cm, over about 11 mS/cm, over about 12 mS/cm, over about 13 mS/cm, over about 14 mS/cm, over about 15 mS/cm, over about 20 mS/cm, or over about 25 mS/cm. In some embodiments, the sample containing the protein is loaded onto the column under conductivity of about 6 mS/cm to about 25 mS/cm or about 8 mS/cm to about 15 mS/cm, or about 9.5 mS/cm to about 14.5 mS/cm, or about 13 mS/cm. In some embodiments, the protein binds to the column and a large amount of impurities do not bind to the column. For example, in some embodiments, the protein binds to the column and about 30% about 40%, about 50%, about 60%, about 70%, about 80%, about 90%, or more of the impurities do not bind to the column.

In some embodiments, the pH of the loaded protein is between 0 and 14.0. In some embodiments, the pH of the loaded protein is between about 3.0 and 10.0. In some embodiments, the pH of the loaded protein is between about 4.0 and 9.0. In some embodiments, the pH of the loaded protein is between about 5.0 and 8.0. In some embodiments, the pH of the loaded protein is about 7.0. In other embodiments, the pH of the loaded protein is about 1.0, about 2.0, about 3.0, about 4.0, about 5.0, about 6.0, about 7.0, about 8.0, about 9.0, about 10.0, about 11.0, about 12.0, about 13.0, or about 14.0. The pH of the sample may be tested and loaded according to methods well known to the skilled person.

In some embodiments, the protein is DNase, and the pH of the loaded sample is between about 4.5 and 14.0. In further embodiments, the protein is DNase and the pH of the loaded sample is between about 6.0 and 8.0. In further embodiments, the protein is DNase and the pH of the loaded sample is about 7.0.

In some embodiments, the column is washed using a very high conductivity, high salt wash buffer to remove bound impurities. The salt in the very high conductivity wash buffer may be selected from, but is not limited to, $(NH_4)_2SO_4$, $Na_2SO_4$, and $CH_3COONa$. In particular embodiments, the very high conductivity wash buffer comprises $(NH_4)_2SO_4$ at a concentration of from about 0.4 M to about 1.5 M. In a further embodiment, the very high conductivity wash buffer comprises $(NH_4)_2SO_4$ at a concentration of from about 0.5 M to about 1.2 M. In a further embodiment, the very high conductivity wash buffer comprises $(NH_4)_2SO_4$ at a concentration of from about 0.6 M to about 1.0 M. In a further embodiment, the very high conductivity wash buffer further comprises $(NH_4)_2SO_4$ at a concentration of about 0.8 M. In another embodiment, the very high conductivity wash buffer further comprises $CaCl_2$ at a concentration of about 0.5 mM to about 1.5 mM. In a further embodiment, the very high conductivity wash buffer further comprises $CaCl_2$ at a concentration of about 1 mM. In some embodiments, the very high conductivity wash buffer comprises 0.8 M $(NH_4)_2SO_4$, 1 mM $CaCl_2$ and 50 mM HEPES.

In some embodiments, the wash with the very high conductivity wash buffer removes bound impurities from the column. For example, in some embodiments, the wash removes at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of the bound impurities.

In some embodiments, the protein is eluted from the column using a very high conductivity, high salt buffer (referred to herein as the elution buffer). The salt in the elution buffer may be selected from, but is not limited to, NaCl, KCl, and NaOAc. In particular embodiments, the elution buffer comprises NaCl at a concentration of from about 0.5 M to about 1.5 M. In a further embodiment, the elution buffer comprises NaCl at a concentration of from about 0.7 M to about 1.3 M. In a further embodiment, the elution buffer comprises NaCl at a concentration of from about 0.9 M to about 1.1 M. In a further embodiment, the elution buffer further comprises NaCl at a concentration of about 1.0 M. In another embodiment, elution buffer further comprises $CaCl_2$ at a concentration of about 0.5 mM to about 1.5 mM. In a further embodiment, elution buffer further comprises $CaCl_2$ at a concentration of about 1 mM. In some embodiments, the elution buffer comprises 1.0 M NaCl, 1 mM $CaCl_2$ and 50 mM HEPES.

In some embodiments, the elution buffer elutes at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of the bound protein of interest.

In some embodiments, the pH of the very high conductivity wash buffer or elution buffer) is between about 5.0 and 9.0. In further embodiments, the pH of the very high conductivity wash buffer or elution buffer is between about 6.0 and 8.0. In further embodiments, the pH of the very high conductivity wash buffer or elution buffer is about 7.0.

In some embodiments, the very high conductivity wash buffer and the elution buffer each have conductivity of over about 70 mS/cm, over about 75 mS/cm, over about 80 mS/cm, over about 85 mS/cm, over about 90 mS/cm, over about 95 mS/cm, or over about 100 mS/cm. In some embodiments, the conductivity of the very high conductivity wash buffer or elution buffer is between about 25 mS/cm and 100 mS/cm, or between about 40 mS/cm and 100 mS/cm, or between about 50 mS/cm and 90 mS/cm, or between about 70 mS/cm and 90 mS/cm. In some embodiments, the very high conductivity wash buffer or elution buffer has conductivity of about 70 mS/cm, about 75 mS/cm, about 80 mS/cm, about 85 mS/cm, about 90 mS/cm, about 95 mS/cm, or about 100 mS/cm.

The very high conductivity wash buffer or elution buffer may comprise any salt that produces the results achieved with the salts exemplified herein. For example, without limitation, the very high conductivity wash buffer may comprise $(NH_4)_2SO_4$, $Na_2SO_4$, $CH_3COONa$, or any salt that can produce similar results. In particular embodiments, the very high conductivity wash buffer comprises $(NH_4)_2SO_4$. The elution buffer may comprise, without limitation, NaCl, KCl, NaOAc, or any salt that produces similar results. In particular embodiments, the elution buffer comprises NaCl. In some embodiments, the very high conductivity wash buffer or elution buffers comprise more than one salt. The person of skill in the art will recognize that the concentrations of $(NH_4)_2SO_4$ and NaCl in the two buffers, or the concentrations of salts equivalent to $(NH_4)_2SO_4$ or NaCl, can be varied to certain extent and still produce similar results.

In some embodiments, the difference in conductivity between the very high conductivity wash buffer and the elution buffer is small. For example, in some embodiments, the very high concentration salt buffer 0.8 M $(NH_4)_2SO_4$ is used as a wash buffer and the very high concentration salt buffer 1.0 M NaCl is used as an elution buffer.

In some embodiments, the methods provided herein further comprise one or more additional wash step, wherein the wash buffer is a low conductivity buffer. For example, in some embodiments, the methods comprise a first wash step wherein the first wash buffer has a low conductivity of less than about 2 mS/cm, or less than about 1 mS/cm, or less than about 0.5 mS/cm. In some embodiments, the first wash buffer has a conductivity of about 0.1 mS/cm to about 5 mS/cm, or about 0.5 mS/cm to about 2 mS/cm, or about 1 mS/cm. In some embodiments, the pH of the low conductivity wash buffer is the same as the pH of the loaded sample. In some embodiments, the pH of the low conductivity wash buffer about 5.0 to about 9.0, or about 6.0 to about 8.0, or about 7.0. In some embodiments, the low conductivity wash buffer comprises $CaCl_2$. In some embodiments, the first wash step removes any remaining unbound impurities. In some embodiments, the methods comprise a first wash step using a low conductivity buffer; a second wash step using a very high conductivity, high concentration salt buffer; and a third wash step using a low conductivity buffer.

In some embodiments, the methods comprise the following steps: loading the sample directly onto the chromatography column under high conductivity of about 9.5 to about 14 mS/cm and at a pH of about 7.0; washing the column with a wash buffer having a low conductivity of about 1 mS/cm and a pH of about 7.0; washing the column with a very high conductivity buffer having a conductivity of about 80 mS/cm or more and a pH of about 7.0; washing the column with a wash buffer having a low conductivity of about 1 mS/cm and a pH of about 7.0; and eluting the protein from the column using a very high conductivity buffer having a conductivity of about 80 mS/cm or more and a pH of about 7.0.

In some embodiments, the methods provided herein comprise adding a detergent to the sample prior to loading the sample on the chromatographic column Detergents are known in the art and include, but are not limited to, t-octylphenoxypolyethoxyethanol (Triton X-100), sodium dodecyl sulfate (SDS), sodium tetradecyl sulfate, sodium hexadecyl sulfate, sodium deoxycholate, polyoxyethylene sorbitan monooleate, and NP40. In some embodiments, the detergent is Triton X-100. Without being bound by theory, the addition of a detergent to the sample effectively inactivate the virus from the sample. The skilled person can readily determine the appropriate amount of detergent to add to the sample according to the methods provided herein. In some embodiments, the final concentration of Triton X-100 in the sample is between about 0.01% and 10%, or between about 0.05% and 5%, or between about 0.1% and 1%, or about 0.5%.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

The term "about", as used herein, refers to plus or minus ten percent of the object that "about" modifies. As used herein, the singular forms "a", "an", and "the" include plural reference unless the context clearly dictates otherwise.

As used herein, the term "low conductivity" refers to conductivity of about 5 mS/cm or less; the term "high conductivity refers to conductivity of about 5 mS/cm to about 25 mS/cm; and the term "very high conductivity" refers to conductivity of above 25 mS/cm, for example at least about 50, at least about 60, at least about 70, or at least about 80 mS/cm.

The present disclosure provides methods for purifying a protein from a cell culture. As used herein, a "cell line" or "cell culture" denotes bacterial, plant, insect or higher eukaryotic cells grown or maintained in vitro. The protein may be produced naturally by the cell or may be produced via recombinant methods. Recombinant methods include genetically altering a host cell by administration of an exogenous polynucleotide, such as a recombinant plasmid or vector. Recombinant methods are well known in the art and described, for example, in (Sambrook et al., 2001) (Molecular Cloning: A Laboratory Manual, 3rd Edition, Cold Spring Harbor Laboratory Press, 2001), and other laboratory textbooks.

Chromatographic materials and methods are known in the art and described, for example, in Chromatography: $6^{th}$ Edition (E. Heftmann, 2004), incorporated herein by reference in its entirety. For example, chromatographic materials useful in the present disclosure include, but are not limited to, mixed mode (e.g., Capto Adhere, Capto MMC, or hydroxyapatite), ion exchange (i.e., cation-exchange, anion-exchange), affinity, hydrophobic interaction, reversed phase, size exclusion, and adsorption materials. The invention also contemplates many support media, including agarose, cellulose, silica, and poly(stryrene-divinylbenzene) (PSDVB). One skilled in the art will also appreciate that the size of the column (i.e., diameter and length) will depend on several factors such as the volume of material to be loaded, the concentration of protein to be purified, and the desired resolution or purity.

Purity of proteins purified using the methods provided herein may be measured by any method known in the art including, but not limited to, reducing or non-reducing sodium dodecyl sulfate polyacrylamide gel electrophoresis (SDS-PAGE), size exclusion chromatography, HPLC (high performance liquid chromatography), capillary electrophoresis, MALDI (Matrix Assisted Laser Desorption Ionization) mass spectrometry, or ELISA (Enzyme Linked Immunosorbent Assay).

All publications cited are incorporated by reference herein in their entirety for all purposes. The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Example 1. Purification of DNase

Recombinant DNase was expressed in a cell culture expressing a DNase gene.

The supernatant of the cell culture was harvested, and Triton X-100 was added to the harvested cell culture fluid (HCCF) to a final concentration of 0.5%. The resulting sample had a pH and conductivity as described in the specification. This Triton X-100 treated sample was loaded onto a mixed mode ion exchange resin, Capto Adhere. Under these conditions, the DNase bound to the resin, and a large amount of impurities did not bind to the resin. Following the load, any remaining unbound impurities were washed from the column with a low conductivity buffer containing 1 mM $CaCl_2$ in pH 7.0, 50 mM HEPES. Bound impurities were removed from the column by washing with a buffer containing 0.8 M $(NH_4)_2SO_4$, 1 mM $CaCl_2$ in pH 7.0, 50 mM HEPES. Following removal of these bound impurities the column was washed with a low conductivity buffer containing 1 mM $CaCl_2$ in pH 7.0, 50 mM HEPES and the DNase was eluted with a buffer containing 1 M NaCl, 1 mM $CaCl_2$ in pH 7.0, 50 mM HEPES. The flow rate was 100 cm/hr.

Figure 2:
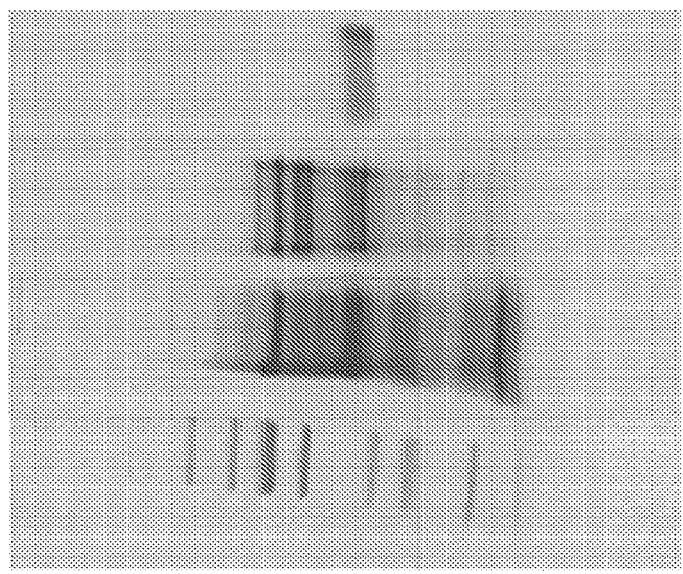
FIG. 2 shows the result of SDS-PAGE analysis of various fractions from the DNase purification experiment. Lane 1 is the marker lane. Lane 2 shows the unbound impurities (impurities not bound to the column). Lane 3 shows the bound impurities washed off from the column by the second wash. Lane 4 shows the eluted DNase.

The results of the study are shown in FIGS. 1 and 2, which demonstrate very high purity of DNase purified from the HCCF. FIG. 1 shows the chromatogram resulting from the experiment. FIG. 2 shows the SDS-PAGE analysis of each fraction. In particular, lane 4 in FIG. 2 shows very high purity of DNase following the elution step.

Together, the results of the study showed that surprisingly, a purification method in which a sample containing DNase can be highly purified using a single chromatographic column and direct loading of the DNase-containing sample onto the column under high conductivity conditions and followed by a very high conductivity wash and a elution using a very high conductivity elution buffer. In part, the results were surprising because the optimal loading conditions for the mixed mode resin were expected to be conditions in which the pH is well below the isoelectric point (pI) of the protein at the load step. However, in the method provided herein, the pH of the load (about 7.0 in the method exemplified herein) was well above the pI of DNase (about 4.0-4.5).

The invention claimed is:

1. A method for purification of a DNase or RNase from a sample comprising:
   loading a sample comprising a DNase or RNase and a detergent onto a chromatography column, washing the column with a wash buffer comprising calcium chloride, wherein the wash buffer has a conductivity of 80 mS/cm or higher, and
   eluting the DNase or RNase from the column with an elution buffer comprising calcium chloride.

2. The method of claim 1, wherein the wash buffer comprises a salt selected from the group consisting of $(NH_4)_2SO_4$, $Na_2SO_4$, and $CH_3COONa$.

3. The method of claim 2, wherein the wash buffer comprises a concentration of about 0.8 M $(NH_4)_2SO_4$.

4. The method of claim 1, wherein the elution buffer has a conductivity of 80 mS/cm or higher.

5. The method of claim 1, wherein the elution buffer comprises a salt selected from the group consisting of NaCl, KCl, and NaOAc.

6. The method of claim 5, wherein the elution buffer comprises a concentration of about 1 M NaCl.

7. The method of claim 1, wherein the method comprises at least two washing steps.

8. The method of claim 7, wherein a first washing step comprises washing the column with a buffer having a conductivity of 2 mS/cm or less.

9. The method of claim 8, further comprising a third washing step, wherein the third washing step comprises washing the column with a buffer having a conductivity of 2 mS/cm or less.

10. The method of claim 1, wherein the DNase is a recombinant DNase.

11. The method of claim 1, wherein the calcium chloride is 1 mM calcium chloride.

12. The method of claim 1, wherein the chromatography column is an ion exchange or a mixed mode chromatography column.

13. The method of claim 12, wherein the mixed mode column is a multimodal anion exchanger.

14. The method of claim 13, wherein the mixed mode column is a Capto Adhere column.

15. The method of claim 1, wherein the sample is a cell culture sample.

16. The method of claim 1, wherein the pH of the loaded sample is between 5.0 and 9.0.

17. The method of claim 16, wherein the pH of the loaded sample is between 6.0 and 8.0.

18. The method of claim 17, wherein the pH of the loaded sample is about 7.0.

19. The method of claim 1, wherein the pH of the loaded sample is the same or higher than the pI of the protein.

20. The method of claim 1, wherein the pH of the wash buffer is between about 5.0 and about 9.0.

21. The method of claim 20, wherein the pH of the wash buffer is about 7.0.

22. The method of claim 1, wherein the pH of the elution buffer is between about 5.0 and about 9.0.

23. The method of claim 22, wherein the pH of the elution buffer is about 7.0.

24. The method of claim 1, wherein the detergent is Triton X-100.

25. The method of claim 24, wherein the detergent is added to the sample at a final concentration of 0.5%.

* * * * *

UNITED STATES PATENT AND TRADEMARK OFFICE
CERTIFICATE OF CORRECTION

PATENT NO. : 10,370,408 B2
APPLICATION NO. : 15/321016
DATED : August 6, 2019
INVENTOR(S) : Gregory Scott Blank et al.

It is certified that error appears in the above-identified patent and that said Letters Patent is hereby corrected as shown below:

On the Title Page

Column 1, Line 2, after "(KY);" delete "Gregory Scott Blank, Menlo Park, CA (US)"

Signed and Sealed this
Twenty-ninth Day of October, 2019

Andrei Iancu
*Director of the United States Patent and Trademark Office*